United States Patent
Lafitte et al.

(10) Patent No.: US 9,523,667 B2
(45) Date of Patent: Dec. 20, 2016

(54) ELECTROCHEMICAL SENSOR SYSTEM

(75) Inventors: Valerie Lafitte, Stafford, TX (US); Gary John Tustin, Sawston (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 407 days.

(21) Appl. No.: 13/584,587

(22) Filed: Aug. 13, 2012

(65) Prior Publication Data

US 2013/0062222 A1   Mar. 14, 2013

(30) Foreign Application Priority Data

Aug. 15, 2011 (GB) .................................. 1113963.1

(51) Int. Cl.
| | | |
|---|---|---|
| *G01N 27/404* | (2006.01) | |
| *G01N 33/28* | (2006.01) | |
| *G01N 27/48* | (2006.01) | |
| *E21B 47/01* | (2012.01) | |
| *E21B 49/08* | (2006.01) | |

(52) U.S. Cl.
CPC ............ *G01N 33/2823* (2013.01); *E21B 47/01* (2013.01); *E21B 49/087* (2013.01); *G01N 27/48* (2013.01)

(58) Field of Classification Search
CPC ...... E21B 47/00; G01N 27/48; G01N 33/2823
USPC ..................................... 205/786.5, 793, 775
See application file for complete search history.

(56) References Cited

U.S. PATENT DOCUMENTS

| | | |
|---|---|---|
| 5,376,254 A | 12/1994 | Fisher |
| 6,287,451 B1 | 9/2001 | Winarta et al. |

FOREIGN PATENT DOCUMENTS

| | | |
|---|---|---|
| WO | 0163094 A1 | 8/2001 |
| WO | 2004011929 A1 | 2/2004 |
| WO | 2004063743 A1 | 7/2004 |
| WO | 2005066618 A1 | 7/2005 |
| WO | 2006057722 A1 | 6/2006 |
| WO | 2010015812 A1 | 2/2010 |

OTHER PUBLICATIONS

Ryabov et al. (J. Phys. Chem. 1995, 99, 14072-14077).*
Jiang et al. (WO 0//63094 A1).*
Rusling (Acc. Chem. Res. 1991, 24, 75-81).*
Mackay et al. (Anal. Chem. 1990, 62, 1084-1090).*

(Continued)

*Primary Examiner* — Luan Van
*Assistant Examiner* — Steven E Rosenwald

(57) ABSTRACT

An electrochemical sensor measuring concentration of an analyte in a test fluid at 50° C. or above by voltammetry uses electrodes in contact with an electrolyte containing the analyte and a redox-active species electrochemically convertible between reduced and oxidised forms. At least one form of the redox active species is present within surfactant micelles. The surfactant micelles enhance thermal stability of the redox active species and may also solubilise a species with poor water solubility, such as t-butylferrocene. A downhole tool incorporating such a sensor comprises a barrier, permeable to the analyte, to separate the electrolyte from subterranean reservoir fluid, so that the sensor directly measures analyte which has passed through the barrier and thereby indirectly measures analyte in the test fluid.

8 Claims, 4 Drawing Sheets

(56) References Cited

OTHER PUBLICATIONS

Ueno et al. (Rev. Phys. Chem. Jap., 1977, 47/1, 25-32).*
Search Report of British Patent Application Serial No. GB1113963.1 dated Nov. 17, 2011: pp. 1-3.
Abbott et al., "Electron Transfer between Amphiphillic Ferrocenes and Electrodes in Cationic Micellar Solution," J. Phys. Chem., 1992, vol. 96: pp. 11091-11095.
Brisset, "Solubilities of Some Electrolytes in Water-Pyridine and Water-Acetonitrile Solvent Mixtures," J. Chem. Eng. Data, 1982, vol. 27: pp. 152-155.
Chen et al., "Electorde reaction of ferrocene in a nitrobenzene + water emulsion," Journal of Electroanalytical Chemistry, 2001, vol. 496: pp. 88-94.
Dayalan et al., "Micelle and Microemulsion Diffusion Coefficients," Electrochemistry in Colloids and Dispersions, Eds. Mackay et al., New York: VCH Publishers, 1992: pp. 119-135.
Kaifer et al., Supramolecular Electrochemistry, New York: Wiley-VCH, 2001: pp. 89-163.
Kamau et al., "Electrochemistry of Bipyridyl Derivatives of Cobalt in Solutions of Anionic and Cationic Micelles," J. Electroanal. Chem., 1987, vol. 233: pp. 173-187.
Kamau et al., "Part III. Reduction of Allyl Halides by Bipyridyl Derivatives of Cobalt in Anionic and Cationic Micelles," J. Electroanal. Chem, 1988, vol. 240: pp. 217-226.
Karásek et al., "Solubility of Solid Ferrocene in Pressurized Hot Water," J. Chem. Eng. Data, 2010, vol. 55: pp. 2866-2869.
Kostela et al., "Electrochemical properties of an amphiphilic viologen in differently charged micelles," Journal of Electroanalytical Chemistry, 2002, vol. 536: pp. 97-107.
Lawrence, "Amperometric Detection of Sulfide: An Electrocatalytic Reaction with Ferrocene Carboxylate," Electroanalysis, 2006, vol. 18(17): pp. 1658-1663.
Lawrence et al., "The Electrochemical Analog of the Methylene Blue Reaction: A Novel Amperometric Approach to the Detection of Hydrogen Sulfide," Electroanalysis, 2000, vol. 12(18): pp. 1453-1460.
Lawrence et al., "Ferrocene sulfonates as electrocatalysts for sulfide detection," Electrochimica Acta, 2006, vol. 52: pp. 499-503.
Lee et al., "Reduction Potentials of N-Hexadecyl-N'-methyl Viologen(2+/+) Solubilized in Cationic, Nonionic, and Anionic Micelles," Langmuir, 1993, vol. 9: pp. 1934-1936.
Löffler et al., "Amperometric biosensors: characterization of dispersed mediator systems," Biosensors & Bioelectronics, 1991, vol. 6: pp. 343-352.
MacKay, "Electrochemistry in association colloids," Colloids and Surfaces A: Physicochemical and Engineering Aspects, 1995, vol. 82: pp. 1-28.
McIntire et al., "Micelles in Analytical Chemistry," Critical Reviews in Analytical Chemistry, 1990, vol. 21(4): pp. 257-278.
Prins et al., "Decomposition of the Ferricenium Cation by Nucleophilic Reagents," Journal of Organometallic Chemistry, 1972, vol. 39: pp. 335-344.
Qutubuddin, "Chapter 21: Electrochemical Studies in Microemulsions," Handbook of Microemulsion Science and Technology, Eds. Kumar et al., New York: Marcel Dekker, Inc., 1999: pp. 651-678.
Rusling, "Electrocatalytic systems organized by micelles," trends in analytical chemistry, 1988, vol. 7(7): pp. 266-269.
Rusling, "Electrochemistry in Micelles, Microemulsions, and Related Microheterogeneous Fluids," Electroanalytical Chemistry vol. 18, Ed. Ballard, New York: Marcel Dekker, Inc., 1994: pp. 1-88.
Rusling et al., "Diffusion of Micelle-Bound Molecules to Electrodes in Solutions of Ionic Surfactants," Anal. Chem. 1988, vol. 60: pp. 1260-1267.
Rusling et al., "Electron transfer in surfactant films on electrodes; copper phthalocyaninetetrasulfonate-didodecyldimethylammonium bromide," Inorganica Chimica Acta, 1994, vol. 226: pp. 159-169.
Rusling et al., "Part 1: Reduction of 4-Bromobiphenyl in Cationic and Non-Ionic Micelles," J. Electroanal. Chem., 1988, vol. 240: pp. 201-216.
Ryabov et al., "Mechanism of a 'Jumping Off' Ferricenium in Glucose Oxidase-D-Glucose-Ferrocene Micellar Electrochemical Systems," J. Phys. Chem., 1995, vol. 99: pp. 14072-14077.
Tustin et al., "Synthesis and characterisation of water soluble ferrocenes: Molecular tuning of redox potentials," Journal of Organometallic Chemistry, 2007, vol. 692: pp. 5173-5182.

* cited by examiner

ELECTROCHEMICAL SENSOR SYSTEM

CROSS-REFERENCE TO RELATED APPLICATION

This application claims priority to British Patent Application Serial No. 1113963.1 filed Aug. 15, 2011, which is incorporated herein by reference in its entirety.

FIELD AND BACKGROUND OF THE INVENTION

This invention relates to electrochemical sensors for determining an analyte in a fluid. There are numerous circumstances in which it is desirable to detect, measure or monitor a constituent of a fluid. Electrochemical sensors may be used for this purpose and the electrochemistry may incorporate a redox-active species whose oxidation and/or reduction is monitored as a part of the analysis.

For instance to measure pH, WO 2005/066618 disclosed an electrochemical sensor in which the electrochemical cell contains two organic compounds which are pH-sensitive redox systems and a ferrocene compound as an internal reference which is not sensitive to pH. To measure sulfide, WO2001/063094 and WO2004/011929 described an approach in which electrochemistry is coupled through a mediator compound to sulfide which is the intended analyte. This mediator compound is present in an electrochemical cell which is exposed to the sulfide. Both in the presence and absence of the sulfide analyte, an electrochemical oxidation and reduction of the mediator compound can take place when appropriate electrical potential is applied to the electrodes. However, one of the redox reactions of the mediator compound can also be brought about through a chemical reaction with the sulfide, and when this takes place there is a measurable change to the electrochemistry. Ferrocene carboxylate and sulfonate were suggested as mediator compounds in Electroanalysis Vol. 18, pages 1658-63 (2006) and in Electrochimica Acta Vol. 52, pages 499-50 (2006). A number of ferrocene sulfonates for possible use in this way have been described in Journal of Organometallic Chemistry Vol. 692, pages 5173-82 (2007). Experimental work in this area has, however, generally been confined to laboratory experiments at ambient temperature.

An issue which can arise in connection with electrochemical analytical systems is the stability of the redox active species employed, in particular stability when exposed to elevated temperatures during use. Exposure to elevated temperature may, however, be unavoidable when using an electrochemical sensor to monitor an industrial process.

One circumstance where there is exposure to temperature arises when carrying out analysis of fluids encountered downhole in a wellbore. Analysis of downhole fluids can be an important aspect of determining the quality and economic value of a hydrocarbon formation and can be applied to save costs and increase production at many stages of oil and gas exploration and production. Some chemical species dissolved in water (for example, $Cl^-$ and $Na^+$) do not change their concentration when moved to the surface and information about their quantities may be obtained at the surface by analysis of downhole samples and in some cases surface samples of a flow. However, the state of chemical species, such as $H^+$ (pH=-log [concentration of $H^+$]), $CO_2$, or $H_2S$ may change significantly while tripping to the surface. The change occurs mainly due to a difference in temperature and pressure between downhole and surface environment. In case of samples taken downhole, this change may also happen due to degassing of a sample (seal failure), mineral precipitation in a sampling bottle, and (especially in case of $H_2S$)—a chemical reaction with the sampling chamber. It should be stressed that pH, $H_2S$ and $CO_2$ are among the most critical parameters for corrosion and scale assessment. Consequently it is of considerable importance to determine their downhole values and there have been proposals for analytical sensors to be used downhole even though this is a difficult environment for an analytical system.

Redox reactions of organic compounds solubilised in surfactant micelles have been examined, in particular for biochemical analyses carried out close to ambient temperature. One instance is Ryabov et al., *J. Phys. Chem.*, Vol. 99, 14072 (1995) which reports voltammetry studies of ferrocene and alkyl-substituted ferrocenes in surfactants, in a biochemical context where the ferrocene redox system is coupled to glucose and glucose oxidase.

SUMMARY OF THE INVENTION

Broadly, we have now found that solubilisation with surfactant is a route to providing redox active species with better thermal stability so that they can be used for analytical procedures at temperatures which are elevated above ambient.

In a first aspect this invention provides an electrochemical sensor for an analyte, capable of use at a working temperature of at least 50° C., comprising a plurality of electrodes in contact with an electrolyte solution containing a redox-active species electrochemically convertible between reduced and oxidised forms wherein the electrolyte solution contains surfactant and at least one of these forms of the redox active species is present within surfactant micelles. This form of the redox active species may be solubilised by the surfactant micelles.

Embodiments of sensor may be used to measure pH generally as disclosed in WO 2005/066618 although with a redox active species entering surfactant micelles. In such a sensor the redox active species which is present within surfactant micelles may be a ferrocene compound as an internal reference which is not sensitive to pH. Embodiments of sensor may be used to measure sulfide using the approach described in WO2001/063094 and WO2004/011929 in which electrochemistry of a redox active species is coupled to sulfide which is the intended analyte. Here too, the redox active species which is present within surfactant micelles may be a ferrocene compound.

The redox active species may be a compound having a low water-solubility so that it could not be dissolved in water at a concentration giving an adequate electrochemical signal. Solubilization by surfactant then increases the concentration in solution and allows the compound to be used. We have observed good stability of such compounds when solubilised in surfactant micelles, outperforming stabilities shown by more soluble redox active compounds without surfactant present.

In a second aspect this invention provides a method of measuring concentration of an analyte, comprising: providing a plurality of electrodes in contact with an electrolyte solution containing the analyte and a redox-active species electrochemically convertible between reduced and oxidised forms wherein the electrolyte solution contains surfactant and at least one of these forms of the redox active species is present within surfactant micelles, and may be solubilised thereby; applying potential to the electrodes and observing current flow as voltage is varied, while the electrolyte solution is at a temperature of at least 50° C.

Electrochemical observation of the redox reaction is preferably carried out by voltammetry, although the stabilisation of a redox active species in accordance with this invention could also be used with other electrochemical techniques.

In some embodiments of this invention, the method may be used to measure analyte in a test fluid which is not itself the electrolyte in contact with the electrodes. This can be done by allowing analyte to migrate from the test fluid into the electrolyte. This may be done by bringing the electrolyte and a test fluid containing the analyte into contact with opposite sides of a barrier, which may be a membrane, which is permeable to the analyte so that analyte can migrate through the barrier. The method can then be used to measure the concentration of analyte in the electrolyte, which will also be an indirect measure of the analyte concentration in the test fluid.

We have observed that surfactant micelles enhance stability of a redox active species when exposed to elevated temperatures. In some embodiments of this invention a sensor and/or method are used at a working temperature which is at least 75° C. and possibly at least 100° C. or 125° C.

This invention may be employed in a diverse range of applications, including equipment for testing fluids at above-ambient temperatures the Earth's surface. However, an area of application which is of particular interest is in devices to be used downhole in a well for testing subterranean fluids. It is normal that temperatures prevailing downhole are higher than ambient temperature at the surface.

Thus, some embodiments of sensor may be incorporated in a downhole tool for measuring an analyte below ground. So in a third aspect this invention provides a downhole tool incorporating an electrochemical sensor for an analyte in a subterranean fluid, capable of use at a downhole temperature of at least 50° C., comprising an enclosure for an electrolyte solution, a plurality of electrodes in contact with an electrolyte solution in the enclosure and a barrier, permeable to the analyte, to separate the electrolyte solution from the subterranean fluid but allow analyte to migrate through the barrier into the electrolyte in the enclosure, wherein the electrolyte contains a redox-active species electrochemically convertible between reduced and oxidised forms and also contains surfactant and at least one of these forms of the redox active species is present within surfactant micelles (and may be solubilised thereby). A sensor or downhole tool embodying this invention may comprise, or be used together with, control means to apply varying potential to the electrodes and measure current flow through the electrolyte. This control means may record applied potential and current at each applied potential, and/or it may record the potential(s) at which current flow is at a maximum.

Downhole measurement tools for oilfield applications are known as such. An electro-chemical technique using a sensor in accordance with the present invention can be applied for example as part of a production logging tool or an open hole formation tester tool for use in a well drilled for oil or gas. In such a case, the invention may be used in providing a downhole real-time water sample validation or downhole pH or sulfide measurement which in turn can be used for predicting mineral scale and for corrosion assessment. Such tools may be devices lowered into a well by means of a cable, such as wireline or slickline, or may be tools carried into a well by coiled tubing, or even tools which are positioned downhole for a longer period.

Downhole measurement tools are also used in wells drilled to monitor groundwater or to access subterranean aquifers. A sensor in accordance with the invention can be utilised in such tools, notably in providing real time measurement of pH and/or oxygen content.

DETAILED DESCRIPTION

Figure 1:
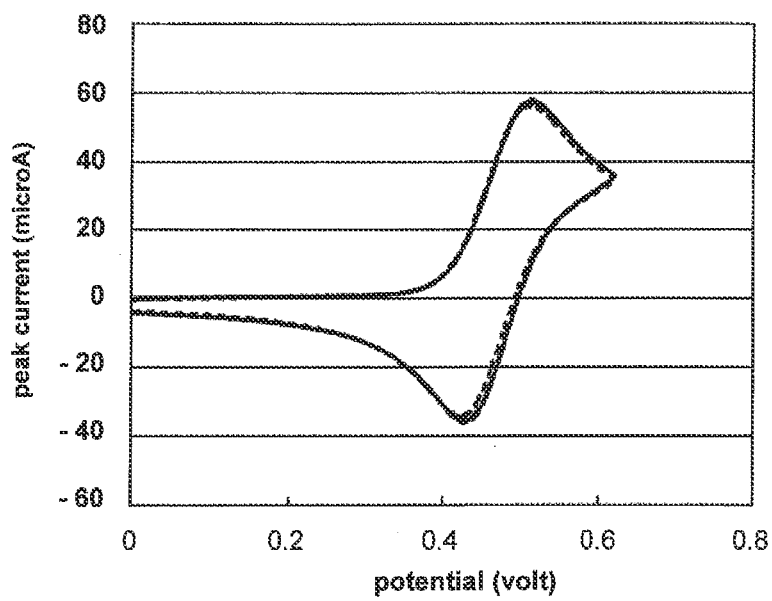
FIG. 1 shows the results of cyclic voltammetry applied to a heat treated sample and a control, in Example 2.

As set forth above, this invention utilises a redox active species and surfactant. These are used in an electrochemical sensor. The redox active species may, in some forms of this invention be a compound with a water solubility of not more than 0.5 mmole/liter at 25° C., possibly not more than 0.2 or 0.1 mmole/liter. In some forms of this invention the redox-active species comprises a metallocene, which may bear substituent groups on its organic rings. The redox-active species may comprise ferrocene which may bear substituent groups. More specifically, ferrocene may be substituted with at least one substituent group which reduces its water solubility relative to the water solubility of ferrocene itself (which has been reported as $4.25 \times 10^{-2}$ mmole/liter). Such a substituent group may possibly be an alkyl or alkenyl group and may be an alkyl group of 1 to 6 carbon atoms or an alkenyl group of 2 to 6 carbon atoms. Groups containing 3 to 6 carbon atoms may be straight chain or branched.

The redox-active species may be a molecule which undergoes a single oxidation and reduction. However, it is possible, within the scope of this invention to employ a molecule which undergoes more than one redox reaction or to employ a polymer or oligomer with a number of redox active sites in the same molecule.

The surfactant may be anionic, non-ionic, cationic or amphoteric or may comprise a mixture of surfactant types. Desirably the surfactant is chosen to solubilise the redox-active species within micelles. For ferrocene and water-insoluble substituted ferrocene compounds we have found that cationic surfactant is suitable.

The surfactant may comprise one or more cationic surfactants of general formula

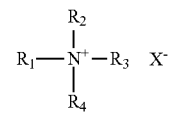

where $R_1$ is a saturated or unsaturated, linear or branched aliphatic chain of at least 10 carbon atoms; $R_2$, $R_3$ and $R_4$ are each independently a linear or branched saturated aliphatic chain of 1 to 3 carbon atoms, preferably a $CH_3$ or a $CH_2CH_3$ group, or a linear or branched saturated aliphatic chain of at least 1 to 3 carbon atoms with one or more of the hydrogen atoms replaced by a hydroxyl group, e.g. —$CH_2CH_2OH$ (hydroxyethyl); or $R_2$ and $R_3$ may together be an alkylene chain of 4 to 6 carbon atoms so that N, $R_2$ and $R_3$ form an aliphatic ring; and $X^-$ is an anion such as a halide. $R_1$ may have up to 24 carbon atoms, such as from 12 to 18 carbon atoms and may be interrupted by an ether oxygen atom. Examples of such surfactants are dodecyltrimethylammonium bromide (DTAB) and cetyltrimethylammonium bromide (CTAB).

The surfactant may comprise one or more anionic surfactants. An anionic surfactant may incorporate an alkyl chain of at least 9 carbon atoms, possibly 12 to 18 carbon atoms and an ionic headgroup. Neutral and zwitterionic surfactants may also incorporate a hydrophobic alkyl chain of such length, with a polar or zwitterionic headgroup.

We have observed that surfactant micelles can usefully enhance thermal stability of ferrocene and derivatives, even up to 125° C. or 150° C., indicating that micelles containing ferrocene are intact up to such temperatures.

The redox reaction may be observed electrochemically by applying potential to the electrodes and observing current flow with sufficient time for reaction between the mediator compound and the analyte, for thereby enabling observation of the concentration of the analyte species present. More specifically, the application of potential may be carried out as cyclic voltammetry in which the potential applied to a working electrode is cycled over a sufficient range to bring about the oxidation and reduction reactions while recording the current flow as the potential is varied. Such cyclic voltammetry has been described and exemplified in Electroanalysis Vol. 12, page 1453 (2000), and in later documents, including WO2004/063743. The recorded current shows peaks at the potentials associated with the reduction and oxidation reactions.

Cyclic voltammetry is normally carried out using an electrochemical cell with three electrodes: a working electrode, a counter electrode and a reference electrode. A varying potential relative to the reference electrode is applied to the working electrode. Cyclic voltammetry is customarily performed with a potential which is varied linearly from a lower limit value to an upper limit value and then back again after which the cycle may be repeated. The potential changes sufficiently slowly that electrochemically oxidised mediator compound is able to come into contact with analyte within the electrolyte. Potential which changes in steps rather than continuously can possibly be employed as an alternative, provided the steps are long enough for steady-state conditions to be established before a subsequent step in potential. It is also possible that this variation in potential whilst recording current flow could be carried out over only a portion of the reduction and oxidation cycle. This would be classed as linear scan voltammetry.

The direct measurement from the procedure is the current flow as potential is applied. The values of particular interest are peak values of current flow together with the applied potentials at which these peaks of current occur. However, it is also possible for the data obtained throughout a cyclic voltammetry experiment to be used as input to a computer program for modelling the chemical processes which occur.

EXAMPLE 1

A number of experimental tests were carried out. Three substituted ferrocene derivatives were used: these were 1,1'-diethylferrocene and vinylferrocene, which are both solids, and t-butylferrocene which is a liquid. Saturated micelle solutions of each ferrocene derivative were prepared by adding the ferrocene derivative to a solution of 2 wt % DTAB in de-ionised water until the solution became saturated and a small undissolved excess of the ferrocene derivative could be seen. With the two solid compounds, the solution was then filtered through a 0.2 µm filter syringe device in order to remove the excess of solid material. In the case of t-butylferrocene which is a liquid, the aqueous surfactant solution was decanted off, leaving the excess of material at the bottom of the flask.

Saturated micelle solutions were each split into multiple samples which were then purged for 5 min with nitrogen in order to remove air. Some of these samples were placed in closed, pressure tight bottles and heated in an oven to 125° C. or 150 ° C. for 24 or 48 hours. Control samples were not heated but were kept in the dark for the same amounts of time.

After subjecting the samples to heat treatments in this way, voltammetry measurements were made using an electrochemical cell with three electrodes which were a working electrode (Boron Doped Diamond or Edged Plane Pyrolitic Graphite), a reference electrode (silver electrode) and a counter electrode (Platinum). Electrochemical measurements were recorded using an PGSTAT30 potentiostat (Ecochemie, Netherlands) using a scanning rate of 0.1V/second. The Boron Doped Diamond (BDD) working electrode was used for the samples treated for 24 hours. The Edged Plane Pyrolitic Graphite (EPPG) working electrode was used for the samples treated for 48 hours.

The oxidative peak current was recorded for each sample. The extent of destruction of the ferrocene compounds was calculated as $$\% \text{ degradation} = \frac{Iref - Isol}{Iref} * 100\%$$

where, Iref corresponds to the oxidative peak current obtained using a control sample and Isol corresponds to the oxidative peak current obtained using a heat treated sample.

All measurements were made in duplicate. The following results were obtained.

| Treatment | 1,1'-diethyl ferrocene | | t-butyl ferrocene | | vinyl ferrocene | |
|---|---|---|---|---|---|---|
| | current (µA) | degradation (%) | current (µA) | degradation (%) | current (µA) | degradation (%) |
| 24 hours at room temp. | 21.72 | | 27.13 | | 10.52 | |
| 24 hours at 125° C. | 22.93 | 0% | 26.86 | 1% | 10.29 | 2.2% |
| 24 hours at 150° C. | 21.73 | 0% | 26.36 | 2% | 9.29 | 11.7% |
| 48 hours at room temp. | 23.95 | | 29.30 | | 10.65 | |

-continued

| Treatment | 1,1'-diethyl ferrocene | | t-butyl ferrocene | | vinyl ferrocene | |
|---|---|---|---|---|---|---|
| | current ($\mu$A) | degradation (%) | current ($\mu$A) | degradation (%) | current ($\mu$A) | degradation (%) |
| 48 hours at 125° C. | 24.19 | 0% | 29.21 | 0% | 9.98 | 6.3% |
| 48 hours at 150° C. | 24.16 | 0% | 27.6 | 5.8% | 8.31 | 22% |

EXAMPLE 2

The procedure of Example 1 was repeated using a solution of t-butylferrocene in 2 wt % DTAB in a pH7 phosphate buffer. FIG. 1 shows (as a solid line) the voltammogram obtained with a sample heated to 150° C. for 24 hours superimposed on the voltammogram obtained with a control sample (broken line). It will be seen that the curve obtained with the heat treated sample is almost indistinguishable from the control. The conclusion is that there was no observable degradation over 24 hours even at 150° C.

Figure 2:
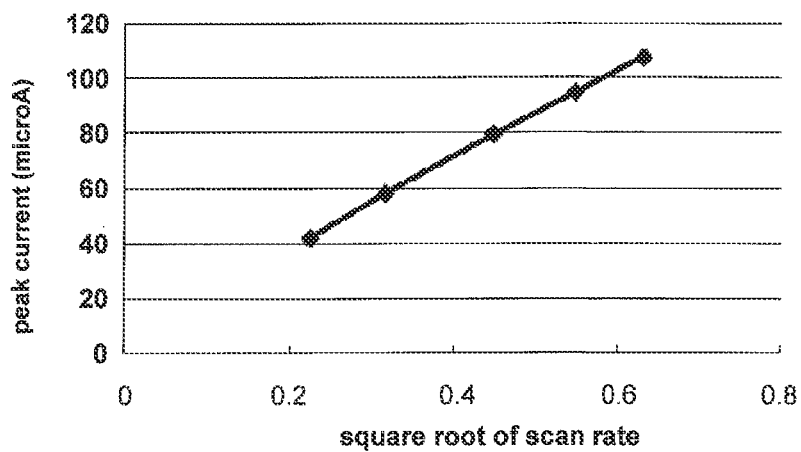
FIG. 2 shows a plot of oxidative peak current against square root of scan rate.

Voltammetry was carried out at a number of scan rates. FIG. 2 shows a plot of oxidative peak current against square root of scan rate. The plot is a straight line which is evidence that the oxidative and reductive processes are both diffusion controlled.

EXAMPLE 3

This example demonstrates the coupling of concentration to the voltammetric response of vinyl ferrocene in micellar solution.

A micellar solution of vinyl ferrocene in a solution of 2 wt % DTAB in deionised water was made as in Example 1 and subjected to 150° C. for 43 hours. A 0.05 molar solution of sodium sulphide in water was prepared. This solution was added by 20 $\mu$L or 40 $\mu$L increments to 10 mL of the micellar solution of vinyl ferrocene. After each addition, the voltammetric response was recorded as in Example 1 using a BDD electrode.

Figure 3A:
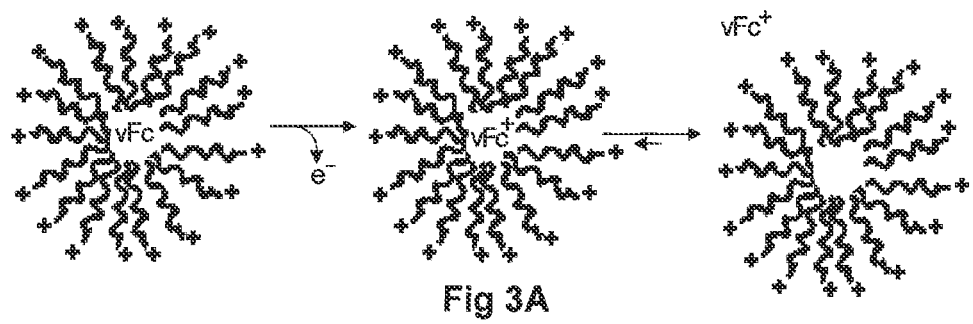
FIGS. 3A and 3B illustrate electrochemical reaction coupled to reduction of bisulfide ion.
Figure 3B:
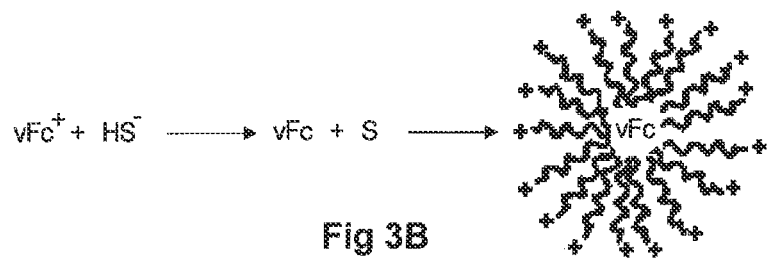

The observed voltammetric response is similar in form to voltammetry observed with ferrocene compounds in the presence of sulfide when surfactant is absent. It is consistent with the vinylferrocene undergoing an electrochemical oxidative process and the oxidized form being reduced back to vinylferrocene by reaction with bisulfide ion. A proposed mechanism for this is illustrated by FIGS. 3A and 3B. As shown at the left of FIG. 3A, vinylferrocene (vFc) is contained within surfactant micelles which have the cationic headgroups of surfactant molecules at their exterior. The vinylferrocene is oxidized electrochemically to the vinylferrocinium cation. It is energetically favorable for this cation to migrate out of the micelles into the aqueous solution as illustrated at the right of FIG. 3A. In solution, the vinylferrocinium cation is reduced back to vinylferrocene by reaction with HS$^-$ ion in the aqueous solution, as shown by FIG. 3B and the vinylferrocene then returns to the interior of a surfactant micelle.

Figure 4:
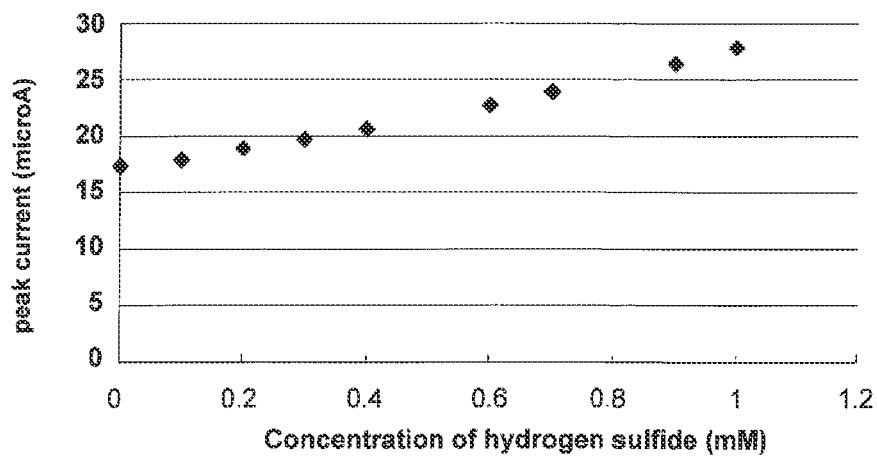
FIG. 4 shows a plot of peak current in cyclic voltammetry applied to a solutions containing increasing sulfide concentration.

FIG. 4 is a plot of oxidative peak current against hydrogen sulfide concentration. It can be seen that peak current increases linearly with sulfide concentration.

EXAMPLE 4

An experimental test, similar to that in Example 1 above, was carried out using the anionic surfactant sodium dodecyl sulfate and using t-butylferrocene as the ferrocene derivative. A saturated micelle solution of t-butylferrocene was prepared by adding the ferrocene derivative to a solution of 2 wt % DTAB in de-ionised water until the solution became saturated and a small undissolved excess of the t-butylferrocene could be seen. The solution was then filtered through a 0.2 $\mu$m filter syringe device.

The saturated micelle solution was split into several samples which were then purged for 5 min with nitrogen in order to remove air. Some of these samples were placed in closed, pressure tight bottles and heated in an oven to 125° C. or 150° C. for 30 hours. Control samples were not heated but were kept in the dark for the same amounts of time.

After subjecting the samples to heat treatments in this way, voltammetry measurements were made as in Example 1 using a BDD working electrode. The following results (mean of duplicate experiments) were obtained.

| Treatment | current ($\mu$A) | degradation (%) |
|---|---|---|
| 30 hours at room temp. | 52.7 | |
| 30 hours at 125° C. | 50.66 | 3.8% |
| 30 hours at 150° C. | 39.73 | 24.5% |

Downhole Tools

Figure 5:
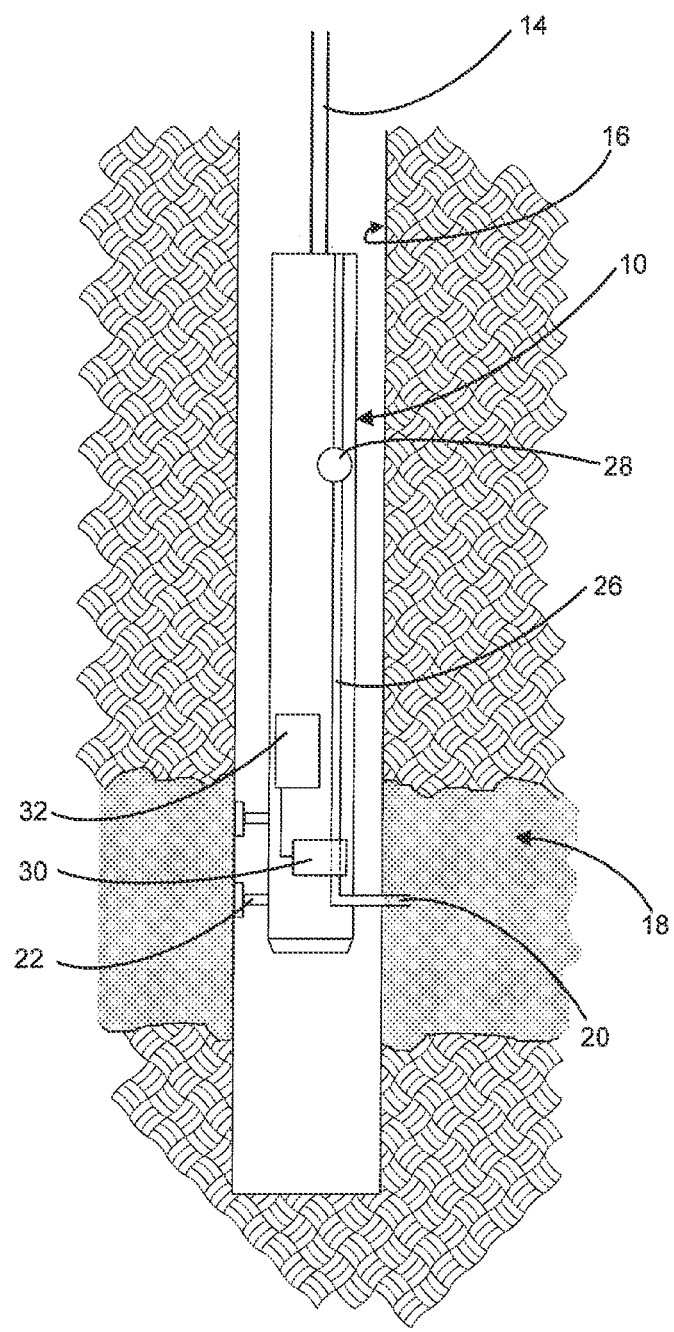
FIG. 5 is a schematic representation of a wellbore tool which is positioned in a wellbore.
Figure 6:
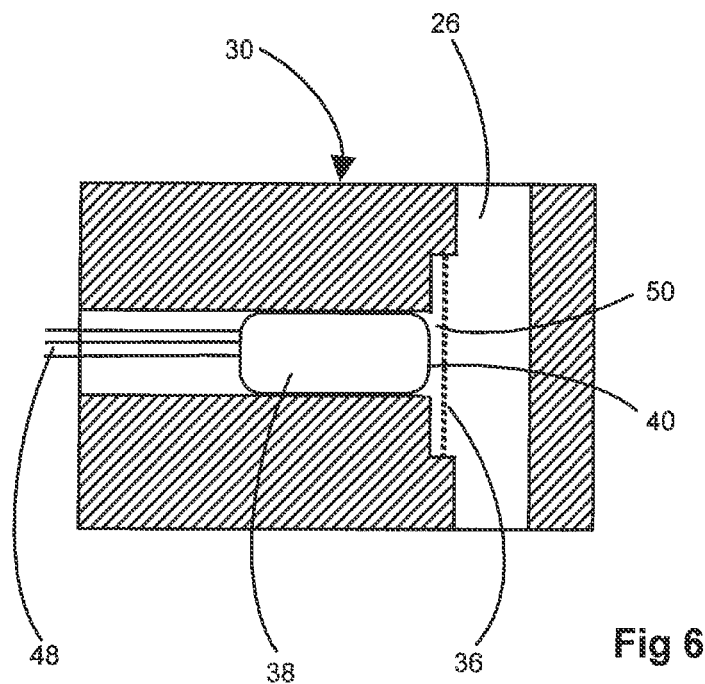
FIG. 6 is a schematic cross sectional view of the electrochemical sensor within the tool of FIG. 5.
Figure 7:
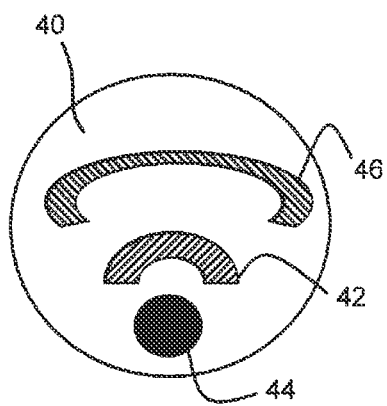
FIG. 7 shows the electrodes on one face of an electrode assembly within the sensor of FIG. 6.

FIGS. 5 to 7 illustrate equipment used to perform the method of the invention below ground, within a wellbore. The tool 10 comprises an elongate substantially cylindrical body which is suspended on a wireline 14 in the wellbore 16, adjacent an earth formation 18 believed to contain recoverable hydrocarbons. The tool is provided with a radially projecting sampling probe 20. The sampling probe 20 is placed into firm contact with the formation 18 by hydraulically operated rams 22 projecting radially from the tool on the opposite side from the sampling probe 20 and is connected to a conduit 26 within the tool. A pump 28 within the tool 10 can be used to draw a sample of the hydrocarbons into the conduit 26. The pump 28 is controlled from the surface at the top of the wellbore via the wireline 14 and control circuitry (not shown) within the tool. The conduit 26 leads through an electrochemical sensor 30 located close to the sampling probe 20.

The sensor 30 is shown rather schematically in cross section in FIGS. 6 and 7. It may be constructed as described in greater detail in WO2004/063743 and/or WO2005/066618. The sensor 30 is generally cylindrical. A flowpath for the fluid whose sulfide content is to be determined extends through the sensor 30 and forms part of the conduit 26. A gas permeable membrane 36 separates this flow path from an axial bore through the sensor, within which an electrode assembly 38 is located. This assembly 38 comprises an insulating body, having three electrodes on its face 40 shown in FIG. 7, namely a working electrode 42 made from boron-doped diamond, a reference electrode 44 in the form of a silver dot coated with silver chloride or silver iodide, and a counter electrode 46 comprising a printed platinum track. The electrodes 42, 44, 46 are connected via respective electrical conductors molded into and extending axially through the body of the electrode assembly 38 to respective electrical leads 48, which connect the sensor 30 to control circuitry 32 within the tool. The enclosed space 50 between the face 40 of the electrode assembly and the membrane 36 is filled with a polar electrolyte which may be an aqueous solution in which a ferrocene compound, which may be t-butylferrocene, vinylferrocene or diethylferrocene as discussed above, are present in micellar surfactant solution.

Once the tool is in place, fluid is drawn through the conduit 26 by the pump 28. Hydrogen sulfide in the fluid can pass through the membrane 36 into the electrolyte in the space 50. After a time for equilibrium to be reached, the control unit 32 (possibly on command received via the wireline 14) applies varying potential to the electrodes and meters the current flowing. This is done as cyclic voltammetry with a scan rate which is slow enough to allow time for reaction between the mediator compound and the sulfide which has entered the electrolyte. The current flowing and the applied potential may be communicated to the surface in real time via the wireline 14 or may be recorded until the tool is retrieved to the surface.

The invention claimed is:

1. A method of measuring concentration of hydrogen sulfide or thiol analyte in a subterranean test fluid at a temperature of 50° to 125° C. in a well comprising:

providing a plurality of electrodes in contact with an electrolyte solution containing a redox-active species electrochemically convertible between reduced and oxidized forms, wherein the electrolyte solution contains surfactant and at least one said form of the redox active species is present within surfactant micelles; and bringing the electrolyte and a test fluid containing the analyte into contact with opposite sides of a membrane, which is permeable to the hydrogen sulfide or thiol analyte so that analyte can migrate through the membrane into the electrolyte solution; and applying potential to the electrodes and observing current flow as voltage is varied;

wherein the redox-active species comprises ferrocene which is substituted with at least one substituent group which is an alkyl group of 1 to 6 carbon atoms or an alkenyl group of 2 to 6 carbon atoms such that the water solubility of the substituted ferrocene is less than the water solubility of unsubstituted ferrocene; and wherein the substituted ferrocene is solubilized by the surfactant micelles.

2. A method according to claim 1 wherein application of potential and observation of current obtains a voltammetric response.

3. A method according to claim 1 which comprises bringing the test fluid into contact with a barrier which separates the test fluid from said electrolyte but which is permeable to the hydrogen sulfide or thiol so that hydrogen sulfide or thiol can migrate into said electrolyte through the barrier.

4. A method according to claim 1 wherein the surfactant is cationic.

5. A method according to claim 1 wherein the surfactant is anionic.

6. A method according to claim 1 wherein the redox-active species is 1,1-diethyl ferrocene.

7. A method according to claim 1 wherein the redox-active species is t-butyl ferrocene.

8. A method according to claim 1 wherein the redox-active species is vinyl ferrocene.

* * * * *